US006485907B1

(12) United States Patent
Beck et al.

(10) Patent No.: US 6,485,907 B1
(45) Date of Patent: Nov. 26, 2002

(54) PCR-BASED DETECTION OF *RHIZOCTONIA CEREALIS*

(75) Inventors: James Joseph Beck, Cary, NC (US); Charles Jason Barnett, Hillsborough, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/481,293

(22) Filed: Jan. 11, 2000

(51) Int. Cl.$^7$ .......................... C12Q 1/68; C12P 19/34; C07H 21/04

(52) U.S. Cl. ......................... 435/6; 435/91.2; 536/23.1; 536/24.3

(58) Field of Search .................. 435/6, 91.2; 536/23.1, 536/24.3

(56) References Cited

U.S. PATENT DOCUMENTS 5,585,238 A * 12/1996 Ligon et al. .................. 435/6

FOREIGN PATENT DOCUMENTS

| | | | |
|---|---|---|---|
| EP | 0955381 A2 | 11/1999 | ............ C12Q/1/68 |
| WO | WO 99/42609 | 8/1999 | ............ C12Q/1/68 |

OTHER PUBLICATIONS

Mazzola Et al., "Virulence of Rhizoctonia oryzae and R. solani AG–8 on Wheat and Detection of r. oryzae in plant tissue by PCR," Phytopathology 86:354–360 (1996).

Turner et al., "Visual disease and PCT assessment of stem base diseases in winter wheat," Plant Pathology 48:742–748 (1999).

Database EMBL online! Accession No. AF063019, Travanty et al., "Application of nuclear rDNA sequences for detection of fungal pathogens of turfgrass," (XP–002167321) May 18, 1999.

Database EMBL Online! Accession No. TCAB3, Kuninaga S., "Rhizoctonia solani genes for 18S rDNA", (XP–002167322) Dec. 28, 1996.

Database EMBL Online! Accession No. TCAB19, Kuninaga S., "Rhizoctonia solani genes for 18S rDNA", (XP–002167323) Dec. 28, 1996.

Database EMBL Online! Accession No. TCAB21, Kuninaga S., "Rhizoctonia solani genes for 18S rDNA", (XP–002167324), Dec. 28, 1996.

Database EMBL Online! Accession No. TCAB22, Kuninaga S., "Rhizoctonia solani genes for 18S rDNA", (XP–002167325), Dec. 28, 1996).

Database EMBL Online! Accession No. TCU7742, Salazar et al., "Thanatephorus cucumeris 23R03 ITS1 and ITS2" (XP–002167326) Mar. 6, 1997.

Database EMBL Online! Accession No. TCAJ202, Johanson A., "Thanatephorus cucumeris 5.8S rRNA gene and internal transcribed spacers 1 and 2", (SP–002167327) Jul. 25, 1997.

Nazar et al, Physiological and Molecular Plant Pathology, vol. 39, pp. 1–11, Oct. 1991.*

Accession No. AF063019, May 1998.*

Bardsley, E.S. et al., "The use of a polymerase chain reaction diagnostic test to detect and estimate the severity of stem base diseases in winter wheat," The 1998 Brighton Conference—Pests & Diseases, 9D–10: pp. 1041–1046 (1998).

Nicholson, P. and Parry, D.W., "Development and use of a PCR assay to detect *Rhizoctonia cerealis*, the cause of sharp eyespot in wheat," Plant Pathology, 45: pp. 872–883 (1996).

White, T.J. et al., "Amplification and Direct Sequencing of Fungal Ribosomal RNA Genes for Phylogenetics," PCR Protocols: A Guide to Methods and Applications: pp. 315–322 (1990).

Travanty, E.A. et al., Genbank Accession No. AF063019 (1998).

* cited by examiner

*Primary Examiner*—W. Gary Jones
*Assistant Examiner*—Jehanne Souaya
(74) *Attorney, Agent, or Firm*—J. Timothy Meigs; Mary Kakefuda

(57) ABSTRACT

Internal Transcribed Spacer (ITS) DNA sequences from the ribosomal RNA gene region are described for different strains of the wheat fungal pathogen, *Rhizoctonia cerealis*. Specific primers from within these sequences are identified as being useful for the identification of *Rhizoctonia cerealis* using PCR-based techniques.

15 Claims, No Drawings

PCR-BASED DETECTION OF *RHIZOCTONIA CEREALIS*

FIELD OF THE INVENTION

The present invention relates to the use of species-specific primers in polymerase chain reaction assays for the detection of *Rhizoctonia cerealis*, a fungal pathogen of wheat. The use of these primers enables the monitoring of disease development in plant populations.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack. However, despite 1 billion worth of expenditure on fungicides, worldwide crop losses amounted to approximately 10% of crop value in 1981 (James, 1981; *Seed Sci. & Technol.* 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981; *Proc.* 1981 *Brit. Crop Prot. Conf.*) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and *Mycosphaerella fijiensis* to triazoles to mention just a few (Jones and Clifford; Cereal Diseases, John Wiley, 1983).

Wheat is currently the most important agricultural commodity in international markets and occupies about 20% of the world's farmed land (1977; Compendium of Wheat Diseases, Amer. Phytopath. Soc. page 1). Eightly percent of the world's supply of wheat is grown in North America, Europe, China, and the Soviet Union. Approximately 20% of the worldwide production of wheat is lost to disease annually.

Sharp eyespot is caused by *Rhizoctonia cerealis* van der Hoeven (teleomorph *Ceratobasidium cereale* Murray & Burpee) and occurs on wheat, barley, oat and rye (1977; Compendium of Wheat Diseases, Amer. Phytopath. Soc. Page 50). Some isolates of the pathogen are also capable of infecting turfgrass causing yellow patch. Severe wheat infections cause premature ripening and lodging, thereby effecting yield. There are presently no known sharp eyespot-resistant cultivars.

In view of the above, there is a real need for the development of technology that will allow the identification of specific fungal pathogens early in the infection process. By identifying the specific pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

The present invention is drawn to methods of identification of different pathotypes of plant pathogenic fungi. The invention provides Internal Transcribed Spacer (ITS) DNA sequences that show variability between different fungal pathotypes. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

In a preferred embodiment, the invention provides ITS1 and ITS2 DNA sequences (e.g., SEQ ID NO:17–26) for the pathogen *Rhizoctonia cerealis*. In another preferred embodiment, the invention provides ITS-derived diagnostic primers (e.g., SEQ ID NO:7–16) for the detection of *Rhizoctonia cerealis*.

This invention provides the possibility of assessing potential damage in a specific crop variety-pathogen strain relationship and of utilizing judiciously the diverse armory of fungicides that is available. Furthermore, the invention can be used to provide detailed information on the development and spread of specific pathogen races over extended geographical areas. The invention provides a method of detection that is especially suitable for diseases with a long latent phase.

Kits useful in the practice of the invention are also provided. The kits find particular use in the identification of the fungal pathogen *Rhizoctonia cerealis*.

BRIEF DESCRIPTION OF THE SEQUENCES IN THE SEQUENCE LISTING

SEQ ID NO:1 Oligonucleotide Primer ITS 1.
SEQ ID NO:2 Oligonucleotide Primer ITS2.
SEQ ID NO:3 Oligonucleotide Primer ITS3.
SEQ ID NO:4 Oligonucleotide Primer ITS4.
SEQ ID NO:5 M13 Universal-20 Primer.
SEQ ID NO:6 Reverse Primer used in Example 2.
SEQ ID NO:7 Oligonucleotide Primer JB643.
SEQ ID NO:8 Oligonucleotide Primer JB644.
SEQ ID NO:9 Oligonucleotide Primer JB645.
SEQ ID NO:10 Oligonucleotide Primer JB646.
SEQ ID NO:11 Oligonucleotide Primer JB647.
SEQ ID NO:12 Oligonucleotide Primer JB648.
SEQ ID NO:13 Oligonucleotide Primer JB649.
SEQ ID NO:14 Oligonucleotide Primer JB650.
SEQ ID NO:15 Oligonucleotide Primer JB687.
SEQ ID NO:16 Oligonucleotide Primer JB688.
SEQ ID NO:17 DNA sequence of the ITS region PCR-amplified from *R. cerealis* isolate 44235, comprising in the 5' to 3' direction: 3' end of the small subunit rRNA gene (nucleotides 1–30), Internal Transcribed Spacer 1 (nucleotides 31–242), 5.8S rRNA gene (nucleotides 244–395), Internal Transcribed Spacer 2 (nucleotides 397–630), and 5' end of the large subunit rRNA gene (nucleotides 631–687).

SEQ ID NO:18 DNA sequence of the ITS region PCR-amplified from *R. cerealis* isolate AGDC57, comprising in the 5' to 3' direction: 3' end of the small subunit rRNA gene (nucleotides 1–30), Internal Transcribed Spacer 1 (nucleotides 31–242), 5.8S rRNA gene (nucleotides 243–395), Internal Transcribed Spacer 2 (nucleotides 396–629), and 5' end of the large subunit rRNA gene (nucleotides 630–686).

SEQ ID NO:19 DNA sequence of the ITS region PCR-amplified from *R. cerealis* isolate CAG1BN1, comprising in the 5' to 3' direction: 3' end of the small subunit rRNA gene (nucleotides 1–30), Internal Transcribed Spacer 1 (nucleotides 31–243), 5.8S rRNA gene (nucleotides 244–396), Internal Transcribed Spacer 2 (nucleotides 397–630), and 5' end of the large subunit rRNA gene (nucleotides 631–687).

SEQ ID NO:20 DNA sequence of the ITS region PCR-amplified from *R. cerealis* isolate AGDC73, comprising in the 5' to 3' direction: 3' end of the small subunit rRNA gene (nucleotides 1–30), Internal Transcribed Spacer 1 (nucleotides 31–241), 5.8S rRNA gene (nucleotides 242–394), Internal Transcribed Spacer 2 (nucleotides 395–628), and 5' end of the large subunit rRNA gene (nucleotides 629–685).

SEQ ID NO:21 DNA sequence of the ITS region PCR-amplified from *R. cerealis* isolate 52182, comprising in the 5' to 3' direction: 3' end of the small subunit rRNA gene (nucleotides 1–30), Internal Transcribed Spacer 1 (nucleotides 31–243), 5.8S rRNA gene (nucleotides 244–396), Internal Transcribed Spacer 2 (nucleotides 397–630), and 5' end of the large subunit rRNA gene (nucleotides 631–687).

SEQ ID NO:22 DNA sequence of the ITS region PCR-amplified from *R. cerealis* isolate Bn505, comprising in the 5' to 3' direction: 3' end of the small subunit rRNA gene (nucleotides 1–30), Internal Transcribed Spacer I (nucleotides 31–243), 5.8S rRNA gene (nucleotides 244–396), Internal Transcribed Spacer 2 (nucleotides 397–630), and 5' end of the large subunit rRNA gene (nucleotides 631–686).

SEQ ID NO:23 DNA sequence of the ITS region PCR-amplified from *R. cerealis* isolate R88–303, comprising in the 5' to 3' direction: 3' end of the small subunit rRNA gene (nucleotides 1–30), Internal Transcribed Spacer 1 (nucleotides 31–243), 5.8S rRNA gene (nucleotides 244–396), Internal Transcribed Spacer 2 (nucleotides 397–630), and 5' end of the large subunit rRNA gene (nucleotides 631–687).

SEQ ID NO:24 DNA sequence of the ITS region PCR-amplified from *R. cerealis* isolate 52184, comprising in the 5' to 3' direction: 3' end of the small subunit rRNA gene (nucleotides 1–30), Internal Transcribed Spacer 1 (nucleotides 31–240), 5.8S rRNA gene (nucleotides 241–393), Internal Transcribed Spacer 2 (nucleotides 394–627), and 5' end of the large subunit rRNA gene (nucleotides 628–684).

SEQ ID NO:25 DNA sequence of the ITS region PCR-amplified from *R. cerealis* isolate 62063, comprising in the 5' to 3' direction: 3' end of the small subunit rRNA gene (nucleotides 1–30), Internal Transcribed Spacer I (nucleotides 31–242), 5.8S rRNA gene (nucleotides 243–395), Internal Transcribed Spacer 2 (nucleotides 396–629), and 5' end of the large subunit rRNA gene (nucleotides 630–686).

SEQ ID NO:26 DNA sequence of the ITS region PCR-amplified from *R. cerealis* isolate 52183, comprising in the 5' to 3' direction: 3' end of the small subunit rRNA gene (nucleotides 1–30), Internal Transcribed Spacer I (nucleotides 31–242), 5.8S rRNA gene (nucleotides 243–395), Internal Transcribed Spacer 2 (nucleotides 396–629), and 5' end of the large subunit rRNA gene (nucleotides 630–686).

SEQ ID NO:27 GenBank sequence (accession #AF063019) listing of DNA sequence of the ITS region from *R. cerealis*, comprising in the 5' to 3' direction: 3' end of the small subunit rRNA gene (nucleotides 1–29), Internal Transcribed Spacer 1 (nucleotides 30–241), 5.8S rRNA gene (nucleotides 242–394), Internal Transcribed Spacer 2 (nucleotides 395–628), and 5' end of the large subunit rRNA gene (nucleotides 629–685).

SEQ ID NO:28 DNA sequence of the ITS region PCR-amplified from *P. herpotrichoides* isolate R1, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:29 DNA sequence of the ITS region PCR-amplified from *S. nodorum* isolate 24425, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:30 DNA sequence of the ITS region PCR-amplified from *S. tritici* isolate 26517, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:31 DNA sequence of the ITS region PCR-amplified from *P. tritici-repentis* isolate 6715, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:32 DNA sequence of the ITS region PCR-amplified from *F. culmorum* isolate 62215, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.

SEQ ID NO:33 DNA sequence of the ITS region PCR-amplified from *M. nivale* isolate 520, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.

DETAILED DESCRIPTION OF THE INVENTION

The present invention provides unique DNA sequences that are useful in identifying different pathotypes of plant pathogenic fungi. Particularly, the DNA sequences can be used as primers in PCR-based analysis for the identification of fungal pathotypes. The DNA sequences of the invention include the Internal Transcribed Spacer (ITS) sequences of the ribosomal RNA gene regions of particular fungal pathogens as well as primers derived from these regions that are capable of identifying the particular pathogen. These ITS DNA sequences from different pathotypes within a pathogen species or genus, which vary between the different members of the species or genus, can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991; *Applied and Environ. Microbiol.* 57: 553–556), and random amplified polymorphic DNA (i.e. RAPD) markers were able to distinguish numerous races of *Gremmeniella abietina*, the causal agent of scleroderris canker in conifers. U.S. Pat. No. 5,585,238 (incorporated herein by reference in its entirety) describes primers derived from the ITS sequences of the ribosomal RNA gene region of strains of *Septoria, Pseudocercosporella*, and *Mycosphaerella* and their use in the identification of these fungal isolates using PCR-based techniques. In addition, WO 95/29260 (herein incorporated by reference in its entirety) describes primers derived from the ITS sequences of the ribosomal RNA gene region of strains of Fusarium and their use in the identification of these fungal isolates using PCR-based techniques. Furthermore, U.S. Pat. No. 5,800,997 (incorporated herein by reference in its entirety) describes primers derived from the ITS sequences of the ribosomal RNA gene region of strains of *Cercospora, Helminthosporium, Kabatiella, and Puccinia* and their use in the identification of these fungal isolates using PCR-based techniques.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units, each of which encodes three mature subunits of 18S (small subunit), 5.8S, and 28S (large subunit). These subunits are separated by two Internal Transcribed Spacers, ITS1 and ITS2, of around 300 bp (White et al., 1990; In: PCR Protocols; Eds.: Innes et al.; pages 315–322). In addition, the transcriptional units are separated by non-transcribed spacer sequences (NTSs). The ITS and NTS sequences are particularly suitable for the detection of specific pathotypes of different fungal pathogens.

The DNA sequences of the invention are from the Internal Transcribed Spacer sequences of the ribosomal RNA gene region of different plant pathogens. The ITS DNA sequences from different pathotypes within a pathogen species or genus vary among the different members of the species or genus. Once having determined the ITS sequences of a pathogen, these sequences can be aligned with other ITS sequences. In this manner, primers can be derived from the ITS sequences. That is, primers can be designed based on regions within the ITS sequences that contain the greatest differences in sequence among the fungal pathotypes. These sequences and primers based on these sequences can be used to identify specific pathogens.

Particular DNA sequences of interest include ITS DNA sequences from *Rhizoctonia cerealis*. Such ITS DNA sequences are disclosed in SEQ ID NOs: 17–26. Sequences of representative oligonucleotide primers derived from these ITS sequences are disclosed in SEQ ID NOs: 7–16. The sequences find use in the PCR-based identification of the pathogen of interest.

Methods for the use of the primer sequences of the invention in PCR analysis are well known in the art. For example, see U.S. Pat. Nos. 4,683,195 and 4,683,202, as well as Schlesser et al. (1991) *Applied and Environ. Microbiol.* 57:553–556. See also, Nazar et al. (1991; *Physiol. and Molec. Plant Pathol.* 39: 1–11), which used PCR amplification to exploit differences in the ITS regions of *Verticillium albo-atrum* and *Verticillium dahliae* and therefore distinguish between the two species; and Johanson and Jeger (1993; *Mycol. Res.* 97: 670–674), who used similar techniques to distinguish the banana pathogens *Mycosphaerella fijiensis* and *Mycospharella musicola.*

The ITS DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications*, Innes et al. (Eds.); pages 282–287.

Alternatively, the ITS sequences of interest can be determined by PCR amplification. In an exemplified embodiment, primers to amplify the entire ITS region are designed according to White et al. (1990; In: PCR Protocols; Eds.: Innes et al. pages 315–322), and the amplified ITS sequence are subcloned into the pCR2.1 cloning vector. The subcloned sequence include the left hand ITS (ITS 1), the right hand ITS (ITS2), as well as the centrally located 5.8S rRNA gene. This is undertaken for several isolates of *Rhizoctonia cerealis.*

The determined ITS sequences are compared within each pathogen group to locate divergences that might be useful to test in PCR to distinguish the different species and/or strains. Exemplary determined ITS DNA sequences are shown in SEQ ID NOs: 17–26. A comparative alignment is made of these ITS DNA sequences. From the identification of divergences, numerous primers are synthesized and tested in PCR-amplification. Templates used for PCR-amplification testing are firstly purified pathogen DNA, and subsequently DNA isolated from infected host plant tissue. Thus, it is possible to identify pairs of primers that are diagnostic, i.e. that identify one particular pathogen species or strain but not another species or strain of the same pathogen.

Preferred primer combinations are able to distinguish between the different species or strains in infected host tissue, i.e. host tissue that has previously been infected with a specific pathogen species or strain. This invention provides numerous primer combinations that fulfill this criterion for detection of *Rhizoctonia cerealis*. The primers of the invention are designed based on sequence differences among the fungal ITS regions. A minimum of one base pair difference between sequences can permit design of a discriminatory primer. Primers designed to a specific fungal DNA's ITS region can be used in combination with a primer made to a conserved sequence region within the ribosomal DNA's coding region to amplify species-specific PCR fragments. In general, primers should have a theoretical melting temperature between about 60 to about 70 degree ° C. to achieve good sensitivity and should be void of significant secondary structure and 3' overlaps between primer combinations. Primers generally have 100% sequence identity with at least about 5–10 contiguous nucleotide bases of ITS 1 or ITS2. In preferred embodiments, primers are anywhere from approximately 5–30 nucleotide bases long.

The present invention lends itself readily to the preparation of "kits" containing the elements necessary to carry out the process. Such a kit may comprise a carrier being compartmentalized to receive in close confinement therein one or more container, such as tubes or vials. One of the containers may contain unlabeled or detectably labeled DNA primers. The labeled DNA primers may be present in lyophilized form or in an appropriate buffer as necessary.

One or more containers may contain one or more enzymes or reagents to be utilized in PCR reactions. These enzymes may be present by themselves or in admixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show typical experimental protocols that can be used in the isolation of ITS sequences, the selection of suitable primer sequences, the testing of primers for selective and diagnostic efficacy, and the use of such primers for disease and fungal isolate detection. Such examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular (*1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Fungal Isolates and Genomic Fungal DNA Extraction

See Table 1 for a listing of the fungal isolates used and their source. Fungi are grown in 150 ml potato dextrose broth inoculated with mycelial fragments from PDA (Potato Dextrose Agar) cultures. Cultures are incubated on an orbital shaker at 28° C. for 7–11 days. Alternatively, mycelia are isolated directly from a PDA plate. Mycelia are pelleted by centrifugation and then ground in liquid nitrogen, and total genomic DNA is extracted using the protocol of Lee and Taylor (1990; In: *PCR Protocols: A Guide to Methods and Applications*; Eds.: Innes et al; pages 282–287).

TABLE 1

Source of Test Isolates

| Isolate | Organism | Source | Origin |
|---|---|---|---|
| 44235 | *Rhizoctonia cerealis* | ATCC[1] | Germany |
| AGDC57 | *Rhizoctonia cerealis* | M. Cubeta[2] | Japan |
| CAGBN1 | *Rhizoctonia cerealis* | M. Cubeta[2] | Georgia, USA |
| AGDC73 | *Rhizoctonia cerealis* | M. Cubeta[2] | Japan |
| 52182 | *Rhizoctonia cerealis* | ATCC[1] | Ohio, USA |
| Bn505 | *Rhizoctonia cerealis* | L. Burpee[3] | Georgia, USA |
| R88/303 | *Rhizoctonia cerealis* | S. Edwards[4] | Cambridge, UK |
| 52184 | *Rhizoctonia cerealis* | ATCC[1] | Ohio, USA |
| 62063 | *Rhizoctonia cerealis* | ATCC[1] | Japan |
| 52183 | *Rhizoctonia cerealis* | ATCC[1] | Ohio, USA |
| 44234 | *Rhizoctonia cerealis* | ATCC[1] | Netherlands |
| 24425 | *Septoria nodorum* | ATCC[1] | Montana |
| 308 | *Pseudocercosporella herpotrichoides*-R type | Novartis[5] | — |
| 5391 | *Fusarium culmorum* | P. Nelson[6] | Germany |
| 36885 | *Fusarium graminearum* | ATCC[1] | Finland |
| 520 | *Microdochium nivale* | Novartis[5] | — |
| — | *Rhizoctonia solani* | Novartis[7] | Florida, USA |

TABLE 1-continued

Source of Test Isolates

| Isolate | Organism | Source | Origin |
|---|---|---|---|
| 44643 | *Pseudocercosporella herpotrichoides*-W type | ATCC[1] | Germany |
| 26517 | *Septoria tritici* | ATCC[1] | Minnesota |
| 6715 | *Pyrenophora tritici-repentis* | ATCC[1] | — |
| 11404 | *Drechslera sorokiniana* | ATCC[1] | Minnesota |
| 60531 | *Cladosporium herbarum* | ATCC[1] | New Zealand |
| 52476 | *Cercospora arachidicola* | ATCC[1] | Oklahoma |
| 36570 | *Pyrenophora teres* | ATCC[1] | Denmark |
| 18222 | *Microdochium nivale* | ATCC[1] | Scotland |
| wf-7-98 | *Rhizoctonia solani* | Ocamb[8] | Oregon, USA |
| wf-9a-98 | *Rhizoctonia solani* | Ocamb[8] | Oregon, USA |
| wf-9b-98 | *Rhizoctonia solani* | Ocamb[8] | Oregon, USA |
| wf-36a-98 | *Rhizoctonia solani* | Ocamb[8] | Oregon, USA |
| R-9367 | *Fusarium graminearum* | P. Nelson[6] | Iran |
| 42040 | *Pseudocercosporella herpotrichoides*-W type | ATCC[1] | — |
| R1 | *Pseudocercosporella herpotrichoides*-R type | P. Nicholson[9] | Belgium |
| 62215 | *Fusarium culmorum* | ATCC[1] | Switzerland |
| 93 | *Microdochium nivale* var. *majus* | Novartis[5] | — |
| R-9420 | *Fusarium graminearum* | P. Nelson[6] | Washington, USA |

[1]American Type Culture Collection, Rockville, Maryland, USA
[2]Dr. Marc Cubeta, North Carolina State University, Raleigh, North Carolina, USA
[3]Dr. Lee Burpee, University of Georgia, Athens, Georgia, USA
[4]Dr. Simon Edwards, Harper Adams Agricultural College, Newport, Shropshire, UK
[5]Novartis Crop Protection AG, CH-4002 Basel, Switzerland
[6]Dr. Paul Nelson, Penn State University, Pennsylvania, USA
[7]Novartis, Vero Beach, Florida, USA
[8]Dr. Cynthia Ocambi, Oregon State University, Corvallis, Oregon, USA
[9]Dr. Paul Nicholson, John Innes Centre, Norwich, UK

Example 2

Isolation of the Internal Transcribed Spacer (ITS) Regions

Approximately 700-bp long internal transcribed spacer region fragments are PCR amplified from 10 ng of genomic DNA isolated from selected fungal isolates listed in Table 1 using 50 pmol of primers ITS 1 (5'-tccgtaggtgaacctgcgg-3'; SEQ ID NO: 1) and ITS4 (5'-tcctccgcttattgatatgc-3'; SEQ ID NO:4). PCRs are performed as described in Example 4. PCR products are cloned using the Invitrogen Corporation's (San Diego, Calif.) TA Cloning Kit (part no. K2000–01) using the PCR2.1 cloning vector. The DNA sequences of the ITS regions are determined by the dideoxy method using the Applied Biosystems (Foster City, Calif.) automated sequencer with the primers ITS1 (SEQ ID NO:1), ITS4 (SEQ ID NO:4), the M13 universal-20 (5'-gtaaaacgacggccagt-3'; SEQ ID NO:5) and Reverse (5'-aacagctatgaccatg-3'; SEQ ID NO:6) primers. The ITS primers ITS1 and ITS4 are detailed in White et al. (1990; In: PCR Protocols; Eds.: Innes et al. pages 315–322).

Example 3

DNA Extraction from Wheat

DNA is extracted from wheat using a bulk maceration method. The bulk maceration method is used to isolate DNA from several naturally infected wheat stems from the field to optimize the field sampling method for high throughput analysis.

Bulk Maceration Method:

(1) Place the appropriate number of 4 cm wheat stem sections cut from the main tiller directly above the basal culm in a Bioreba (Reinach, Switzerland) heavy duty plastic bag (cat#490100). Weigh the plant tissue, plastic bag with stem sections minus the tare (weight of the plastic bag).

(2) Add an equal volume (ml) of Muller Extraction Buffer (0.1% w/v Tween-80; 0.04 M Tris-Cl, pH 7.7; 0.15 M NaCl; 0.1% w/v BSA-Pentex fraction V; 0.01% w/v sodium azide; 200 mM EDTA) per weight (g) of wheat tissue. Macerate the tissue using a Bioreba Homex 6 homogenizer set at 70. Grind the leaves until the tissue is fibrous.

(3) Pool the extracts from multiple bags, if used, and vortex well. Aliquote the extraction juice into eppendorf tubes on ice.

(a) Boil 100 μl of the concentrated extract for 5 minutes.

(b) Place the boiled extract on ice.

(c) Make a 1:10 dilution by adding 10 μl from the boiled, concentrated extract to 90 μl of sterile $dH_2O$.

(d) Store the diluted extracts on ice until ready to use.

Example 4

Polymerase Chain Reaction Amplification

Polymerase chain reactions are performed with the GeneAmp Kit from Perkin-Elmer/Cetus (Norwalk, Conn.; part no. N808-0009) using 50 mM KCl, 2.5 mM $MgCl_2$, 10 mM Tris-HCl, pH8.3, containing 200 μM of each dTTP, dATP, dCTP, and dGTP, 50 pmol each primer, 2.5 units of Taq polymerase and 10 ng of genomic DNA or 1 μl of 1:10 diluted plant extract in a final volume of 50 μl. Reactions are run for 30–40 cycles of 15 s at 94° C., 15 s at 50° C.–70° C., and 45 s at 72° C. in a Perkin-Elmer/Cetus Model 9600 or Model 9700 thermal cycler. The products are analyzed by loading 10 μl of each PCR sample on a 1.0% agarose gel and electrophoresing.

Example 5

Synthesis and Purification of Oligonucleotides

Oligonucleotides (primers) are synthesized by, for example, either Integrated DNA Technologies (Coralville, Iowa) or Midland Certified Reagent Company (Midland, Tex.).

Example 6

Selection of Species-Specific Primers

The ITS region from *R. cerealis* isolate 44234 is aligned with the ITS regions from *S. nodorum, P. herpotrichoides* R-type, *P. tritici-repentis, F. culmorum, M. nivale* and *S. tritici*. Oligonucleotide primers such as those shown below in Table 2 are synthesized according to Example 5 based on analysis of the aligned sequences. Primers are designed to the regions that contain the greatest differences in sequence among the fungal species. An additional alignment is made with the ITS regions from the following *R. cerealis* isolates: 44235, AGDC57, CAGBN1, AGDC73, 52182, Bn505, R88/303 and 52184. Primers are also designed to regions highly conserved among the *R. cerealis* isolates. In addition, the published ribosomal gene-specific primers ITS1, ITS2, ITS3 and ITS4 (White et al., 1990; In: PCR Protocols; Eds.: Innes et al. pages 315–322) are synthesized for testing in combination with the primers specific for the ITS regions.

TABLE 2

| | Primers Designed for Fungal Detection | |
|---|---|---|
| Primer Template | Primer | Primer Sequence |
| 18S rDNA | ITS1 | 5'-tccgtaggtgaacctgcgg-3' (SEQ ID NO:1) |
| 5.8S rDNA | ITS2 | 5'-gctgcgttcttcatcgatgc-3' (SEQ ID NO:2) |
| 5.8S rDNA | ITS3 | 5'-gcatcgatgaagaacgcagc-3' (SEQ ID NO:3) |
| 25S rDNA | ITS4 | 5'-tcctccgcttattgatatgc-3' (SEQ ID NO:4) |
| *R. cerealis* | JB643 | 5'-gcgagagagaggctggct-3' (SEQ ID NO:7) |
| *R. cerealis* | JB644 | 5'-ctcgcgagagagaggctggct-3' (SEQ ID NO:8) |
| *R. cerealis* | JB645 | 5'-gagatcagatcataaagtgtg-3' (SEQ ID NO:9) |
| *R. cerealis* | JB646 | 5'-gagatcagatcataaagtgtgtttg-3' (SEQ ID NO:10) |
| *R. cerealis* | JB647 | 5'-ctgtgcaactgtttagacggtcg-3' (SEQ ID NO:11) |
| *R. cerealis* | JB648 | 5'-tgcaactgtttagacggtcg-3' (SEQ ID NO:12) |
| *R. cerealis* | JB649 | 5'-accgttagaagcggttcgtccat-3' (SEQ ID NO:13) |
| *R. cerealis* | JB650 | 5'-gttagaagcggttcgtccat-3' (SEQ ID NO:14) |
| *R. cerealis* | JB687 | 5'-tgcacctgtttagacggttg-3' (SEQ ID NO:15) |
| *R. cerealis* | JB688 | 5'-tgtgcacctgtttagacggt-3' (SEQ ID NO:16) |

Example 7

Determination of Primer Specificity to Purified Fungal Genomic DNA

PCRs are performed according to Example 4 using different primer combinations (Table 3) in an attempt to amplify a single specific fragment. Specific PCR amplification products are produced from primers designed from the ITS regions between the small and large ribosomal DNA subunits of each fungal strain of interest.

TABLE 3

ITS-Derived Diagnostic PCR Primers

| Primer Specificity | 5' Primer | 3' Primer | Approximate size of amplified fragment |
|---|---|---|---|
| *R. cerealis* | JB648 (SEQ ID NO:12) | JB645 (SEQ ID NO:9) | 523 bp |
| *R. cerealis* | ITS1 (SEQ ID NO:1) | JB646 (SEQ ID NO:10) | 637 bp |
| *R. cerealis* | ITS1 (SEQ ID NO:1) | JB645 (SEQ ID NO:9) | 637 bp |
| *R. cerealis* | ITS1 (SEQ ID NO:1) | JB650 (SEQ ID NO:14) | 596 bp |
| *R. cerealis* | JB648 (SEQ ID NO:12) | ITS4 (SEQ ID NO:4) | 573 bp |
| *R. cerealis* | JB643 (SEQ ID NO:7) | JB645 (SEQ ID NO:9) | 485 bp |
| *R. cerealis* | JB687 (SEQ ID NO:15) | JB645 (SEQ ID NO:9) | 523 bp |
| *R. cerealis* | JB688 (SEQ ID NO:16) | JB645 (SEQ ID NO:9) | 525 bp |
| *R. cerealis* | JB687 (SEQ ID NO:15) | ITS4 (SEQ ID NO:4) | 573 bp |
| *R. cerealis* | JB688 (SEQ ID NO:16) | ITS4 (SEQ ID NO:4) | 575 bp |
| *R. cerealis* | JB687 (SEQ ID NO:15) | JB646 (SEQ ID NO:10) | 523 bp |
| *R. cerealis* | JB688 (SEQ ID NO:16) | JB646 (SEQ ID NO:10) | 525 bp |

Example 8

Determination of Primer Specificity to Plant Tissue Infected with Fungi and Cross-Reactivity with Other Cereal Fungal Pathogens Total genomic DNA is isolated as described in Example 3 from healthy wheat stems and from wheat stems infected with *R. cerealis*. PCRs are performed as described in Example 4 testing primer combinations such as those listed in Table 3 against DNA from the wheat tissue. Purified fungal genomic DNAs are obtained as described in Example I and PCR assayed as described in Example 4 using the diagnostic primers. Other fungal DNA species and isolates are tested for the ability of the diagnostic primers to cross-react therewith.

*R. cerealis*-specific primer combination JB648 (SEQ ID NO: 12) and JB645 (SEQ ID NO:9) amplify a 523 bp fragment from DNA from all of the *R. cerealis* isolates listed in Table 1 and from *R. cerealis*-infected wheat tissue. This primer combination does not amplify a diagnostic fragment from healthy wheat tissue. This primer combination also does not amplify a diagnostic fragment from purified genomic DNA isolated from the following common cereal pathogens: *P. herpotrichoides* R- and W-pathotypes, *D. sorokiniana, C. herbarum, S. tritici, C arachidicola, S. nodorum, R. solani, F. culmorum, F graminearunm, M nivale, P. tritici-repentis* and *P. teres*. Similar diagnostic results are obtained with the other *R. cerealis*-specific primer combinations listed in Table 3.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

What is claimed is:

1. An isolated DNA molecule comprising an Internal Transcribed Spacer sequence selected from the group consisting of:

(a) ITS1 of *Rhizoctonia cerealis*, wherein ITS1 of *Rhizoctonia cerealis* comprises nucleotides 31–243 of SEQ ID NO:17, nucleotides 31–242 of SEQ ID NO:18, nucleotides 31–243 of SEQ ID NO:19, nucleotides 31–241 of SEQ ID NO:20, nucleotides 31–243 of SEQ ID NO:21, nucleotides 31–243 of SEQ ID NO:22, nucleotides 31–180 of SEQ ID NO:23, nucleotides 31–240 of SEQ ID NO:24, nucleotides 31–242 of SEQ ID NO:25, or nucleotides 31–242 of SEQ ID NO:26; and (b) ITS2 of *Rhizoctonia cerealis*, wherein ITS2 of *Rhizoctonia cerealis* comprises nucleotides 397–630 of SEQ ID NO:21, nucleotides 397–630 of SEQ ID NO:22, nucleotides 397–630 of SEQ ID NO:23, nucleotides 394–627 of SEQ ID NO:24, or nucleotides 396–629 of SEQ ID NO:26.

2. An oligonucleotide primer selected from the group consisting of SEQ ID NO's:7–16.

3. A pair of oligonucleotide primers, wherein at least one of said primers is the oligonucleotide primer of claim 2.

4. A pair of oligonucleotide primers according to claim 3, wherein said pair is selected from the following primer pairs:
SEQ ID NO:12 and SEQ ID NO:9,
SEQ ID NO:1 and SEQ ID NO:10,
SEQ ID NO:1 and SEQ ID NO:9,
SEQ ID NO:1 and SEQ ID NO:14,
SEQ ID NO:12 and SEQ ID NO:4,
SEQ ID NO:7 and SEQ ID NO:9,
SEQ ID NO:15 and SEQ ID NO:9,
SEQ ID NO:16 and SEQ ID NO:9,
SEQ ID NO:15 and SEQ ID NO:4,
SEQ ID NO:16 and SEQ ID NO:4,
SEQ ID NO:15 and SEQ ID NO:10, and
SEQ ID NO:16 and SEQ ID NO:10.

5. A pair of oligonucleotide primers according to claim 4, wherein said pair of primers is SEQ ID NO:12 and SEQ ID NO:9.

6. A method for the detection of a fungal pathogen, comprising the steps of:

(a) isolating DNA from a plant leaf infected with a pathogen;

(b) subjecting said DNA to polymerase chain reaction amplification using at least one primer according to claim 2; and (c) detecting said fungal pathogen by visualizing the product or products of said polymerase chain reaction amplification.

7. The method of claim 6, wherein said fungal pathogen is *Rhizoctonia cerealis.*

8. A method for the detection of a fungal pathogen, comprising the steps of:

(a) isolating DNA from a plant leaf infected with a pathogen;

(b) amplifying a part of the Internal Transcribed Spacer sequence of said pathogen using said DNA as a template in a polymerase chain reaction with a pair of primers according to claim 3; and (c) detecting said fungal pathogen by visualizing the amplified part of the Internal Transcribed Spacer sequence.

9. The method of claim 8, wherein said fungal pathogen is *Rhizoctonia cerealis.*

10. A method for the detection of *Rhizoctonia cerealis*, comprising the steps of:

(a) isolating DNA from a plant leaf infected with *Rhizoctonia cerealis;*

(b) amplifying a part of the Internal Transcribed Spacer sequence of *Rhizoctonia cerealis* using said DNA as a template in a polymerase chain reaction with a pair of primers according to claim 4; and (c) detecting *Rhizoctonia cerealis* by visualizing the amplified part of the Internal Transcribed Spacer sequence.

11. The method of claim 10, wherein said pair of primers is SEQ ID NO:12 and SEQ ID NO:9.

12. A diagnostic kit used in detecting a fungal pathogen, comprising the primer of claim 2.

13. A diagnostic kit used in detecting a fungal pathogen, comprising the pair of primers of claim 3.

14. A diagnostic kit used in detecting a fugal pathogen, comprising the pair of primers of claim 4.

15. A diagnostic kit used in detecting a fungal pathogen, comprising the pair of primers of claim 5.

* * * * *

SEQUENCE LISTING

```
<160> NUMBER OF SEQ ID NOS:  33

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: ITS1

<400> SEQUENCE: 1

tccgtaggtg aacctgcgg                                                   19


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: ITS2

<400> SEQUENCE: 2

gctgcgttct tcatcgatgc                                                  20


<210> SEQ ID NO 3
<211> LENGTH: 20
```

-continued

```
<212> TYPE: DNA
<213> ORGANISM: Artificial Sequence
<220> FEATURE:
<223> OTHER INFORMATION: Description of Artificial Sequence: ITS3

<400> SEQUENCE: 3

gcatcgatga agaacgcagc                                                    20


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: ITS4

<400> SEQUENCE: 4

tcctccgctt attgatatgc                                                    20


<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: M13
      Universal 20 Primer

<400> SEQUENCE: 5

gtaaaacgac ggccagt                                                       17


<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Reverse
      Primer

<400> SEQUENCE: 6

aacagctatg accatg                                                        16


<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: JB643

<400> SEQUENCE: 7

gcgagagaga ggctggct                                                      18


<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: JB644

<400> SEQUENCE: 8

ctcgcgagag agaggctggc t                                                  21


<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: JB645
```

-continued

<400> SEQUENCE: 9
gagatcagat cataaagtgt g 21

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: JB646

<400> SEQUENCE: 10
gagatcagat cataaagtgt gtttg 25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: JB647

<400> SEQUENCE: 11
ctgtgcaact gtttagacgg tcg 23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: JB648

<400> SEQUENCE: 12
tgcaactgtt tagacggtcg 20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: JB649

<400> SEQUENCE: 13
accgttagaa gcggttcgtc cat 23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: JB650

<400> SEQUENCE: 14
gttagaagcg gttcgtccat 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: JB687

<400> SEQUENCE: 15
tgcacctgtt tagacggttg 20

<210> SEQ ID NO 16
<211> LENGTH: 20

-continued

<212> TYPE: DNA
<213> ORGANISM: Artificial Sequence
<220> FEATURE:
<223> OTHER INFORMATION: Description of Artificial Sequence: JB688

<400> SEQUENCE: 16
tgtgcacctg tttagacggt 20

<210> SEQ ID NO 17
<211> LENGTH: 687
<212> TYPE: DNA
<213> ORGANISM: Rhizoctonia cerealis

<400> SEQUENCE: 17
tccgtaggtg aacctgcgga aggatcatta atgaaatgaa tgtagagtcg gttgtagctg 60
ggtcttttaa tcgaggccat gtgcacacct tctctttcat ccactcacac ctgtgcacct 120
gtttagacgg ttgaaggaaa aagtctttct cgcgagagag agggccggct ccttttcccg 180
tccaatacat aaaatcttat atatttaatc agaatgtaat cgatgtaaac gcatctataa 240
actaagtttc aacaacggat ctcttggctc tcgcatcgat gaagaacgca gcgaaatgcg 300
ataagtaatg tgaattgcag aattcagtga atcatcgaat ctttgaacgc accttgcgct 360
ccttggtatt cctcggagca cgcctgtttg agtatcatga aattctcaaa gcaagtcttt 420
tgttaattca actggctttt gttttggatt tggaggtttt gcagattcac gtctgctcct 480
cttaaatgca ttagctggat ctctataaaa ccggttccac tcggcgtgat aagtatcact 540
cgctgaggac actcttgaaa aagggtggcc ggattcatgg atgaaccgct tctaacggtc 600
tattagatta gacaaacaca ctttatgatc tgatctcaaa tcaggtggga ctacccgctg 660
aacttaagca tatcaataag cggagga 687

<210> SEQ ID NO 18
<211> LENGTH: 686
<212> TYPE: DNA
<213> ORGANISM: Rhizoctonia cerealis

<400> SEQUENCE: 18
tccgtaggtg aacctgcgga aggatcatta atgaaatgaa tgtagagtcg gttgtagctg 60
ggtcttttaa tcgaggccat gtgcacacct tctctttcat ccactcacac ctgtgcacct 120
gtttagacgg ttgaaggaaa aagtctttct cgcgagagag aggccggctc cttttcccgt 180
ccaatacata aaatcttata tatttaatca gaatgtaatc gatgtaaacg catctataaa 240
ctaagtttca acaacggatc tcttggctct cgcatcgatg aagaacgcag cgaaatgcga 300
taagtaatgt gaattgcaga attcagtgaa tcatcgaatc tttgaacgca ccttgcgctc 360
cttggtattc ctcggagcac gcctgtttga gtatcatgaa attctcaaag caagtctttt 420
gttaattcaa ctggcttttg ttttggattt ggaggttttg cagattcacg tctgctcctc 480
ttaaatgcat tagctggatc tctataaaac cggttccact cggcgtgata agtatcactc 540
gctgaggaca ctcttgaaaa agggtggccg gattcatgga tgaaccgctt ctaacggtct 600
attagattag acaaacacac tttatgatct gatctcaaat caggtgggac tacccgctga 660
acttaagcat atcaataagc ggagga 686

<210> SEQ ID NO 19
<211> LENGTH: 687
<212> TYPE: DNA
<213> ORGANISM: Rhizoctonia cerealis -continued

<400> SEQUENCE: 19
tccgtaggtg aacctgcgga aggatcatta atgaaatgaa tgtagagtcg gttgtagctg 60
ggtcttttaa tcgaggccat gtgcacacct tctctttcat ccactcacac ctgtgcacct 120
gtttagacgg ttgaaggaaa aagtctttct cgcgagagag agggccggct ccttttcccg 180
tccaatacat aaaatcttat atatttaatc agaatgtaat cgatgtaaac gcatctataa 240
actaagtttc aacaacggat ctcttggctc tcgcatcgat gaagaacgca gcgaaatgcg 300
ataagtaatg tgaattgcag aattcagtga atcatcgaat ctttgaacgc accttgcgct 360
ccttggtatt cctcggagca cgcctgtttg agtatcatga aattctcaaa gcaagtcttt 420
tgttgattca actggctttt gttttggatt tggaggtttt gcagattcac gtctgctcct 480
cttaaatgca ttagctggat ctctataaaa ccggttccac tcggcgtgat aagtatcact 540
cgctgaggac actcttgaaa aagggtggcc ggattcatgg atgaaccgct tctaacggtc 600
tattagatta gacaaacaca ctttatgatc tgatctcaaa tcaggtggga ctacccgctg 660
aacttaagca tatcaataag cggagga 687

<210> SEQ ID NO 20
<211> LENGTH: 685
<212> TYPE: DNA
<213> ORGANISM: Rhizoctonia cerealis

<400> SEQUENCE: 20
tccgtaggtg aacctgcgga aggatcatta atgaatgaat gtagagtcgg ttgtagctgg 60
gtcttttaat cgaggccatg tgcacacctt ctctttcatc cactcacacc tgtgcacctg 120
tttagacggt tgaaggaaaa agtctttctc gcgagagaga ggccggctcc ttttcccgtc 180
caatacataa aatcttatat atttaatcag aatgtaatcg atgtaaacgc atctataaac 240
taagtttcaa caacggatct cttggctctc gcatcgatga agaacgcagc gaaatgcgat 300
aagtaatgtg aattgcagaa ttcagtgaat catcgaatct ttgaacgcac cttgcgctcc 360
ttggtattcc tcggagcacg cctgtttgag tatcatgaaa ttctcaaagc aagtcttttg 420
ttaattcaac tggcttttgt tttggatttg gaggttttgc agattcacgt ctgctcctct 480
taaatgcatt agctggatct ctataaaacc ggttccactc ggcgtgataa gtatcactcg 540
ctgaggacac tcttgaaaaa gggtggccgg attcatggat gaaccgcttc taacggtcta 600
ttagattaga caaacacact ttatgatctg atctcaaatc aggtgggact acccgctgaa 660
cttaagcata tcaataagcg gagga 685

<210> SEQ ID NO 21
<211> LENGTH: 687
<212> TYPE: DNA
<213> ORGANISM: Rhizoctonia cerealis

<400> SEQUENCE: 21
tcctccgctt attgatatgc ttaagttcag cgggtagtcc cacctgattt gagatcagat 60
cataaagtgt gtttgtctaa tctaatagac cgttagaagc ggttcgtcca tgaatccggc 120 caccctttttg caagagtgtc ctcagcgagt gatacttatc acgccgagtg gaaccggttt 180
tatagagatc cagctaatgc atttaagagg agcagacgtg aatctgcaag acctccaaat 240
ccaaagcaaa agccagttga attaacaaaa gacttgcttt gagaatttca tgatactcaa 300
acaggcgtgc tccgaggaat accaaggagc gcaaggtgcg ttcaaagatt cgatgattca 360
ctgaattctg caattcacat tacttatcgc atttcgctgc gttcttcatc gatgcgagag 420

-continued

```
ccaagagatc cgttgttgaa acttagttta tagatgcgtt tacatcgatt acattctgat    480
taaatatata agattttatg tattggacgg gaaaaggagc cggccctctc tctcgcgaga    540
aagacttttt ccttcaaccg tctaaacagg tgcacaggtg tgagtggatg aaagagaagg    600
tgtgcacatg gcctcgatta aaagacccag ctacaaccga ctctacattc atttcattaa    660
tgatccttcc gcaggttcac ctacgga                                        687
```

<210> SEQ ID NO 22
<211> LENGTH: 686
<212> TYPE: DNA
<213> ORGANISM: Rhizoctonia cerealis

<400> SEQUENCE: 22

```
tccgtaggtg aacctgcgga aggatcatta atgaaatgaa tgtagagtcg gttgtagctg     60
ggtcttttaa tcgaggccat gtgcacacct tctctttcat ccactcacac ctgtgcacct    120
gtttagacgg ttgaaggaaa aagtctttct cgcgagagag agggccggct ccttttcccg    180
tccaatacat aaaatcttat atatttaatc agaatgtaat cgatgtaaac gcatctataa    240
actaagtttc aacaacggat ctcttggctc tcgcatcgat gaagaacgca gcgaaatgcg    300
ataagtaatg tgaattgcag aattcagtga atcatcgaat ctttgaacgc accttgcgct    360
ccttggtatt cctcggagca cacctgtttg agtatcatga aattctcaaa gcaagtcttt    420
tgttaattca actggctttt gttttggatt tggaggtttt gcagattcac gtctgctcct    480
cttaaatgca ttagctggat ctctataaaa ccggttccac tcggcgtgat aagtatcact    540
cgccgaggac actcttgaaa aagggtggcc ggattcatgg atgaaccgct tctaacggtc    600
tattagatta gacaaacaca ctttatgatc tgatctcaaa tcaggtggga ctacccgctg    660
aacttaagca ttcaataagc ggagga                                         686
```

<210> SEQ ID NO 23
<211> LENGTH: 687
<212> TYPE: DNA
<213> ORGANISM: Rhizoctonia cerealis

<400> SEQUENCE: 23

```
tccgtaggtg aacctgcgga aggatcatta atgaaatgaa tgtagagtcg gttgtagctg     60
ggtcttttaa tcgaggccat gtgcacacct tctctttcat ccactcacac ctgtgcacct    120
gtttagacgg ttgaaggaaa aagtctttct cgcgagagag agggccggct ccttttcccg    180
tccaatacat aaaatcttat atatttaatc agaatgtaat cgatgtaaac gcatctataa    240
actaagtttc aacaacggat ctcttggctc tcgcatcgat gaagaacgca gcgaaatgcg    300
ataagtaatg tgaattgcag aattcagtga atcatcgaat ctttgaacgc accttgcgct    360
ccttggtatt cctcggagca cacctgtttg agtatcatga aattctcaaa gcaagtcttt    420
tgttaattca actggctttt gttttggatt tggaggtctt gcagattcac gtctgctcct    480
cttaaatgca ttagctggat ctctataaaa ccggttccac tcggcgtgat aagtatcact    540
cgccgaggac actcttgcaa aagggtggcc ggattcatgg acgaaccgct tctaacggtc    600
tattagatta gacaaacaca ctttatgatc tgatctcaaa tcaggtggga ctacccgctg    660
aacttaagca tatcaataag cggagga                                        687
```

<210> SEQ ID NO 24
<211> LENGTH: 684
<212> TYPE: DNA

-continued

<213> ORGANISM: Rhizoctonia cerealis

<400> SEQUENCE: 24
tccgtaggtg aacctgcgga aggatcatta atgaatgaat gtagagtcgg ttgtagctgg 60
gtcttttaat cgaggccatg tgcacgcctt ctctttcatc cacacacacc tgtgcacctg 120
tttagacggt cgaaggaaaa agtctttctc gcgagagaga ggctggctcc ttttccgtcc 180
aatacataaa atcttatata tttaatcaga atgtaatcga tgtaaacgca tctataaact 240
aagtttcaac aacggatctc ttggctctcg catcgatgaa gaacgcagcg aaatgcgata 300
agtaatgtga attgcagaat tcagtgaatc atcgaatctt tgaacgcacc ttgcgctcct 360
tggtattcct cggagcacgc ctgtttgagt atcatgaaat tctcaaagca agtcttttgt 420
taattcaact ggcttttgtt ttggatttgg aggtcttgca gattcacgtc tgctcctctt 480
aaatgcatta gctggatctc tataaaatcg gttccactcg gcgtgataag tatcactcgc 540
tgaggacact cttgcaaaag ggtggccgga ttcatggacg aaccgcttct aacggtctat 600
tagattagac aaacacactt tatgatctga tctcaaatca ggtgggacta cccgctgaac 660
ttaagcatat caataagcgg agga 684

<210> SEQ ID NO 25
<211> LENGTH: 686
<212> TYPE: DNA
<213> ORGANISM: Rhizoctonia cerealis

<400> SEQUENCE: 25
tccgtaggtg aacctgcgga aggatcatta atgaaatgaa tgtagagtcg gttgtagctg 60
ggtcttttga tcgaggccat gtgcacacct tctctttcat ccactcacac ctgtgcacct 120
gtttagacgg tcgaaggaaa aagtctttct cgcgagagag aggccggctc cttttcccgt 180
ccaatacata aaatcttata tatttaatca gaatgtaatc gatgtaaacg catctataaa 240
ctaagtttca acaacggatc tcttggctct cgcatcgatg aagaacgcag cgaaatgcga 300
taagtaatgt gaattgcaga attcagtgaa tcatcgaatc tttgaacgca ccttgcgctc 360
cttggtattc ctcggagcac gcctgtttga gtatcatgaa attctcaaag caagtctttt 420
gttaattcaa ctggcttttg ttttggattt ggaggttttg cagattcacg tctgctcctc 480
ttaaatgcat tagctggatc tctataaaac cggttccact cggcgtgata agtatcactc 540
gctgaggaca ctcttgaaaa agggtggccg gattcatgga tgaaccgctt ctaacggtct 600
attagattag acaaacacac tttatgatct gatctcaaat caggtgggac tacccgctga 660
acttaagcat atcaataagc ggagga 686

<210> SEQ ID NO 26
<211> LENGTH: 686
<212> TYPE: DNA
<213> ORGANISM: Rhizoctonia cerealis

<400> SEQUENCE: 26
tccgtaggtg aacctgcgga aggatcatta atgaatgaat gtagagatcg gttgtagctg 60
ggtcttttaa tcgaggccat gtgcacgcct tctctttcat ccacacacac ctgtgcacct 120
gtttagacgg tcgaaggaaa aagtctatct cgagagagag aggccggctc cttttccgtc 180
caatacataa aatccttata tatttaatca gaatgtaatc gatgtaaacg catctataaa 240
ctaagtttca acaacggatc tcttggctct cgcatcgatg aagaacgcag cgaaatgcga 300
taagtaatgt gaattgcaga attcagtgaa tcatcgaatc tttgaacgca ccttgcgctc 360

-continued

```
cttggtattc ctcggagcac gcctgtttga gtatcatgaa attctcaaag caagtctttt    420

gttaattcaa ctggcttttg ctttggattt ggaggtcttg cagattcacg tctgctcctc    480

ttaaatgcat tagctggatc tctataaaac cggttccact cggcgtgata agtatcactc    540

gctgaggaca ctcttgcaaa agggtggccg gattcatgga cgaaccgctt ctaacggtct    600

attagattag acaaacacac tttatgatct gatctcaaat caggtgggac tacccgctga    660

acttaagcat atcaataagc ggagga                                         686


<210> SEQ ID NO 27
<211> LENGTH: 685
<212> TYPE: DNA
<213> ORGANISM: Rhizoctonia cerealis

<400> SEQUENCE: 27

tccgtaggtg aacctgcgga agatcattaa tgaaatgaat gtagagtcgg ttgtagctgg     60

gtcttttaat cgaggccatg tgcacacctt ctctttcatc cactcacacc tgtgcacctg    120

tttagacggt tgaaggaaaa agtctttctc gcgagagaga ggccggctcc ttttcccgtc    180

caatacataa aatcttatat atttaatcag aatgtaatcg atgtaaacgc atctataaac    240

taagtttcaa caacggatct cttggctctc gcatcgatga agaacgcagc gaaatgcgat    300

aagtaatgtg aattgcagaa ttcagtgaat catcgaatct ttgaacgcac cttgcgctcc    360

ttggtattcc tcggagcacg cctgtttgag tatcatgaaa ttctcaaagc aagtcttttg    420

ttaattcaac tggcttttgt tttggatttg gaggttttgc agattcacgt ctgctcctct    480

taaatgcatt agctggatct ctataaaacc ggttccactc ggcgtgataa gtatcactcg    540

ctgaggacac tcttgaaaaa gggtggccgg attcatggat gaaccgcttc taacggtcta    600

ttagattaga caaacacact ttatgatctg acctcaaatc aggtgggact acccgctgaa    660

cttaagcata tcaataagcg gagga                                          685


<210> SEQ ID NO 28
<211> LENGTH: 627
<212> TYPE: DNA
<213> ORGANISM: Pseudocercosporella herpotrichoides

<400> SEQUENCE: 28

tccgtaggtg aacctgcgga aggatcatta atagagcaat ggatagacag cgccccggga     60

gaaatcctgg gggccaccct acttcggtaa ggtttagagt cgtcgggcct ctcggagaag    120

cctggtccag acctccaccc ttgaataaat tacctttgtt gctttggcag ggcgcctcgc    180

gccagcggct tcggctgttg agtacctgcc agaggaccac aactcttgtt tttagtgatg    240

tctgagtact atataatagt taaaactttc aacaacggat ctcttggttc tggcatcgat    300

gaagaacgca gcgaaatgcg ataagtaatg tgaattgcag aattcagtga atcatcgaat    360

ctttgaacgc acattgcgcc ctctggtatt ccgggggggca tgcctgttcg agcgtcatta    420

taaccactca agctctcgct tggtattggg gttcgcgtct tcgcggcctc taaaatcagt    480

ggcggtgcct gtcggctcta cgcgtagtaa tactcctcgc gattgagtcc ggtaggttta    540

cttgccagca acccccaatt ttttacaggt tgacctcgga tcaggtaggg atacccgctg    600

aacttaagca tatcaataag cggagga                                        627


<210> SEQ ID NO 29
<211> LENGTH: 583
<212> TYPE: DNA
```

-continued

<213> ORGANISM: Septoria nodorum

<400> SEQUENCE: 29

```
tccgtaggtg aacctgcgga aggatcatta cactcagtag tttactactg taaaaggggc     60

tgttagtctg tatagcgcaa gctgatgagc agctggcctc ttttatccac ccttgtcttt    120

tgcgtaccca cgtttcctcg gcaggcttgc ctgccggttg gacaaattta taaccttttt    180

aattttcaat cagcgtctga aaaacttaat aattacaact ttcaacaacg gatctcttgg    240

ttctggcatc gatgaagaac gcagcgaaat gcgataagta gtgtgaattg cagaattcag    300

tgaatcatcg aatctttgaa cgcacattgc gccccttggt attccatggg gcatgcctgt    360

tcgagcgtca tttgtaccct caagctctgc ttggtgttgg gtgtttgtcc tctccctagt    420

gtttggactc gccttaaaat aattggcagc cagtgttttg gtattgaagc gcagcacaag    480

tcgcgattcg taacaaacac ttgcgtccac aagccttttt aacttttgac ctcggatcag    540

gtagggatac ccgctgaact taagcatatc aataagcgga gga                      583
```

<210> SEQ ID NO 30
<211> LENGTH: 548
<212> TYPE: DNA
<213> ORGANISM: Septoria tritici

<400> SEQUENCE: 30

```
tccgtaggtg aacctgcgga gggatcatta ccgagcgagg gcctccgggt ccgacctcca     60

accctttgtg aacacatccc gttgcttcgg gggcgaccct gccgggcgcc cccggaggac    120

caccaaaaaa cactgcatct ctgcgtcgga gtttacgagt aaatcgaaac aaaactttca    180

acaacggatc tcttggttct ggcatcgatg aagaacgcag cgaaatgcga taagtaatgt    240

gaattgcaga attcagtgaa tcatcgaatc tttgaacgca cattgcgccc cctggtattc    300

cggggggcat gcccgttcga gcgtcattac accactccag cctcgctggg tattgggcgt    360

cttttcgcgg gggatcactc ccccgcgcgc ctcaaagtct ccggctgagc ggtctcgtct    420

cccagcgttg tggcatcacg tctcgccgcg gagttcacga gccctcacgg ccgttaaatc    480

acacctcagg ttgacctcgg atcgggtagg gatacccgct gaacttaagc atatcaataa    540

gcggagga                                                             548
```

<210> SEQ ID NO 31
<211> LENGTH: 579
<212> TYPE: DNA
<213> ORGANISM: Pyrenophora tritici-repentis

<400> SEQUENCE: 31

```
tccgtaggtg aacctgcgga gggatcatta cacaaatatg aagccggact gggatagggc     60

ctcgctgcct tgcccgtctg gcgccatatt cacccatgtc tttttgcgta ctacttgttt    120

ccttggcggg tccgcccgcc aattggacct tattcaaacc tttttttcag ttgcaatcag    180

cgtcagcaaa acaaatgtaa tcaattacaa ctttcaacaa cggatctctt ggttctggca    240

tcgatgaaga acgcagcgaa atgcgataag tagtgtgaat tgcagaattc agtgaatcat    300

cgaatctttg aacgcacatt gcgccctttg gtattccaaa gggcatgcct gttcgagcgt    360

catttgtacc ctcaagcttt gcttggtgtt gggcgtcttg tctctctccc gagactcgcc    420

ttaaaatcat tggcagccgg cctactggtt tcggagcgca gcacattatt tgcgctcttg    480

tccagccgcg gtcgcgcgtc catgaagctt ctttcaacct tttgacctcg gatcaggtag    540

ggatacccgc tgaacttaag catatcaata agcggagga                           579
```

-continued

```
<210> SEQ ID NO 32
<211> LENGTH: 504
<212> TYPE: DNA
<213> ORGANISM: Fusarium culmorum

<400> SEQUENCE: 32

tgcggaggga tcattaccga gtttacaact cccaaacccc tgtgaacata ccttatgttg     60

cctcggcgga tcagcccgcg ccccgtaaaa agggacggcc cgccgcagga accttaaact    120

ctgtttttag tggaacttct gagtataaaa aacaaataaa tcaawacttt caacaacgga    180

tctcttggtt ctggcatcga tgaagaacgc agcaaaatgc gataagtaat gtgaattgca    240

gaattcagtg aatcatcgaa tctttgaacg cacattgcgc ccgccagtat tctggcgggc    300

atgcctgttc gagcgtcatt tcaaccctca agcccagctt ggtgttggga gctgcagtcc    360

tgctgcactc cccaaataca ttggcggtca cgtcgagctt ccatarcgta gtaatttaca    420

tatcgttact ggtaatcgtc gcggccacgc cgttaaaccc caacttctga atgttgacct    480

cggatcaggt aggaataccc gctg                                           504

<210> SEQ ID NO 33
<211> LENGTH: 526
<212> TYPE: DNA
<213> ORGANISM: Microdochium nivale

<400> SEQUENCE: 33

ggtgaacctg cggagggatc atwactgagt ttwtaactct ccaaaccatg tgaacttacc     60

actgttgcct cggtggatgg tgytgtctct cgggacggtg ccacckcsgg tggacwacct    120

aaactctgtt aatttttgtc aatctgaatc aaactaagma ataagtrarr actwtcwacw    180

acggatctct tggttctggc atcgatgaag aacgcakcga aatgcgataa gtaatgtgaa    240

tygyagaatt cagtgaatca tcgaatcttt gaacgcacat tgcgcccaty agtattctag    300

tgggcatrcc tgttcgagcg tcatttcaac ccttaagcct agcttagtgt tggragactg    360

cctaatacgc agctcctcaa aaccagtggc ggagtcggtt cgtkctctga gcgtagtaat    420

tttttatctc gcttctgcaa gccggactgs caacagccat aaaccgcacc cttcsggggc    480

actttttaat ggttgacctc ggatcaggta ggaatacccg ctgaac                   526
```